United States Patent
Schwindeman et al.

(10) Patent No.: US 6,720,391 B2
(45) Date of Patent: Apr. 13, 2004

(54) FUNCTIONALIZED INITIATORS FOR ANIONIC POLYMERIZATION, PROTECTED FUNCTIONALIZED POLYMERS, DEPROTECTED ANALOGUES THEREOF, AND METHODS OF MAKING THE SAME

(75) Inventors: James Anthony Schwindeman, Gastonia, NC (US); Robert J. Letchford, Cherryville, NC (US); Eric John Granger, Lafayette, IN (US); Roderic P. Quirk, Akron, OH (US)

(73) Assignee: FMC Corporation, Philadelphia, PA (US)

(*) Notice: Subject to any disclaimer, the term of this patent is extended or adjusted under 35 U.S.C. 154(b) by 63 days.

(21) Appl. No.: 10/062,331

(22) Filed: Feb. 1, 2002

(65) Prior Publication Data

US 2003/0023020 A1 Jan. 30, 2003

Related U.S. Application Data

(60) Provisional application No. 60/265,817, filed on Feb. 1, 2001.

(51) Int. Cl.[7] .................................. C08F 8/18
(52) U.S. Cl. ................. 525/355; 525/328.8; 525/328.9; 525/332.8; 525/332.9; 525/333.1; 525/333.2; 525/333.3; 525/333.5; 525/342; 525/353; 525/358.1; 525/359.1; 525/359.4
(58) Field of Search ..................... 525/328.8, 328.9, 525/332.8, 332.9, 333.1, 333.2, 333.3, 333.5, 342, 253, 355, 358.1, 359.1, 359.4

(56) References Cited

U.S. PATENT DOCUMENTS

| 4,473,686 | A | | 9/1984 | Grigo et al. ................. 525/184 |
|---|---|---|---|---|
| 5,340,881 | A | | 8/1994 | Kennedy et al. .......... 525/333.7 |
| 6,107,414 | A | * | 8/2000 | Schwindeman et al. .... 525/355 |
| 6,184,309 | B1 | * | 2/2001 | Schwindeman et al. .... 525/355 |
| 6,221,991 | B1 | * | 4/2001 | Letchford et al. ........ 526/303.1 |
| 6,362,284 | B1 | * | 3/2002 | Schwindeman et al. . 525/328.8 |
| 6,545,103 | B2 | * | 4/2003 | Quirk et al. ................. 525/342 |

FOREIGN PATENT DOCUMENTS

| EP | 1057808 | 12/2000 | ......... C07C/323/12 |
|---|---|---|---|
| WO | WO 9706192 | 8/1997 | ......... C08F/236/10 |
| WO | WO 9802465 | 1/1998 | ............ C08F/19/44 |
| WO | WO 0032645 | 6/2000 | ............. C08F/8/00 |

OTHER PUBLICATIONS

A. Hirao, H. Nagahama, T. Ishizone, S. Nakahama, *Synthesis of Polymers with Carboxy End Groups by Reaction of Polystyryl Anions with 4–Bromo–1,1,1–trimethoxybutane*, Macromolecules, vol. 26, No. 9, pp. 2145–2150, Apr. 26, 1993.

B. Borer, R. Taylor, *Trimethyl 4–Lithioorthobutanoate: Preparation and Synthetic Applications*, Tetrahedron Letters, pp. 601–602, Oct. 1990.

M. Labeau, H. Cramail, A. Deffieux, *End–functionalization of Polystyryl and Polybutadienyl Lithium by Chloroalkyl Derivatives Bearing Oxygen Atoms*, Polymer International, vol. 41, No. 4, pp. 453–462, 1996.

Rowley, Michael et al. "4–Heterocyclylpiperidines as Selective High–Affinity Ligands a the Human Dopamine D4 Receptor" *Journal of Medicinal Chemistry* 40:2374–2385 (1997).

XP 002213730 Database: Section Ch, Week 199227. Derwent Publications Ltd.: London, Great Britain. May 22, 1992.

Borer, Bennett C. and Richard J.K. Taylor. "Trimethyl 4–Lithioorthobutanoate: Preparation and Synthetic Applications" *Letters* Oct.:601–602 (1990).

Cabrera, Gustavo et al. "Triisobutylaluminum (TIBA) as a reagent to convert 2,2–dimethoxyalkanes to 2–methoxy–1–alkenes" *Tetrahedron Letters* 42:5867–5869 (2001).

Chen, Ling–Ching and Huey–Min Wang "De(monothio)actealization Induced by Hypervalent Iodine and Sodium Iodide" *OPPI Briefs* 31(5):562–564 (1999).

Feng, Xiangdong and Mathias O. Senge. "An efficient synthesis of highly functionalized asymmetric porphyrins with organolithium reagents" *Journal of the Chemical Society, Perkins Transactions 1* 1030–1038 (2001).

Huang, Jui–Wen et al. "Magnesium Bromide Promoted Barbier–Type Intramolecular Cyclization of Halo–Substituted Acetals, Ketals, and Orthoesters" *Tetrahedron Letters* 40:8647–8650 (1999).

International Search Report corresponding to PCT/US02/02963 mailed on Oct. 31, 2002.

Irie, Osamu et al. "Further Studies on Total Synthesis of Sarain A. Efforts Toward Annulation of the Macrocyclic Rings" *Journal of Organic Chemistry* 64:587–595 (1999).

Iwabuchi, Y. et al. "An enantio– and stereocontrolled synthesis of (–)–mycestericin E *via cinchona* alkaloid–catalyzed asymmetric Baylis–Hillman reaction" *Chemical Communications* 2032–2031 (2001).

Noda, Yoshihiro and Hitoshi Kashin. "Synthesis of Both Enantiomers of Four Different Macrocyclic Lactones" *Heterocycles* 48(1):5–10 (1998).

* cited by examiner

*Primary Examiner*—Helen L. Pezzuto
(74) *Attorney, Agent, or Firm*—Myers Bigel Sibley & Sajovec, PA

(57) ABSTRACT

The present invention provides functionalized electrophiles, their analogous initiators, and processes for preparing these compounds. The present invention also relates to homotelechelic, heterotelechelic, and radial functional polydiene polymers, polyarylene polymers and polydiene/polyarylene copolymers, their optionally hydrogenated analogues, their optionally deprotected analogues, and processes for preparing these functionalized polymers.

17 Claims, No Drawings

FUNCTIONALIZED INITIATORS FOR ANIONIC POLYMERIZATION, PROTECTED FUNCTIONALIZED POLYMERS, DEPROTECTED ANALOGUES THEREOF, AND METHODS OF MAKING THE SAME

CROSS-REFERENCE TO RELATED APPLICATIONS

This application is related to commonly assigned copending provisional application Serial No. 60/265,817, filed Feb. 1, 2001, the entire disclosure of which is hereby incorporated by reference, and claims the benefit of its earlier priority date under 35 USC Section 119(e).

FIELD OF THE INVENTION

The present invention relates to novel functionalized electrophiles, their analogous initiators, and processes for preparing these compounds. The present invention also relates to homotelechelic, heterotelechelic, and radial functional polydiene polymers, polyarylene polymers and polydiene/polyarylene copolymers, their optionally hydrogenated analogues, their optionally deprotected analogues, and processes for preparing these functionalized polymers.

BACKGROUND OF THE INVENTION

Terminal functionalization of living polymer anions with various electrophiles has been extensively studied. See, for example, U.S. Pat. Nos. 3,786,116 and 4,409,357. More recently, Hirao and Nakahama have introduced the concept of functionalization with an electrophile that contains a protected functional group. This group can then be removed from the polymer ("deprotection") in a subsequent step. For examples of protected electrophiles in the synthesis of functionalized polymers, see K. Ueda, A. Hirao, and S. Nakahama, Macromolecules, 23, 939 (1990) and M. Tokyamo, A. Hirao, S. Nakahama and K. Takenaka, Macromol. Chem. Phys., 197, 3135 (1996).

Recently, protected acetal and carboxylic acid electrophiles were disclosed, see M. P. Labeau, H. Cramail, and A. Deffieux, Polymer International, 41, 453 (1996) and A. Hirao, H. Nakahama, T. Ishizone, and S. Nakahama, Macromolecules, 26, 2145 (1993), respectively. The articles report polymerizing styrene using butyl lithium to form the living polymer anion. Using the protected acetal and carboxylic acid electrophiles, the resulting polymers included a protected functionality at one end of the polymer chain.

SUMMARY OF THE INVENTION

The present invention provides novel compounds useful as electrophiles for incorporating a protected functionality into a living polymer anion. In particular the electrophiles incorporate a protected carbonyl or carboxyl group into a living polymer. The electrophiles are represented by the formula:

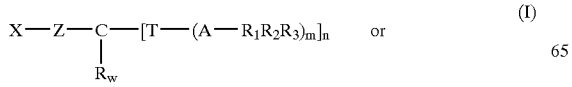

(I)

-continued

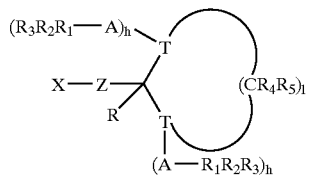

(II)

wherein:
each X is independently halogen, preferably selected from the group consisting of chloride, bromide and iodide;
each Z is independently a branched or straight chain hydrocarbon connecting group which contains 1–25 carbon atoms, optionally substituted with aryl or substituted aryl;
each T is independently selected from the group consisting of oxygen, sulfur, nitrogen, and mixtures thereof;
$(A\!-\!R_1R_2R_3)$ is a protecting group, in which each A is independently an element selected from Group IVa of the Periodic Table of the Elements; and $R_1$, $R_2$, and $R_3$ are each independently selected from the group consisting of hydrogen, alkyl, substituted alkyl, aryl, substituted aryl, cycloalkyl, and substituted cycloalkyl;
R, $R_4$, and $R_5$ are each independently selected from the group consisting of hydrogen, alkyl, substituted alkyl, aryl, substituted aryl, cycloalkyl and substituted cycloalkyl;
h is 0 when T is oxygen or sulfur, and 1 when T is nitrogen;
l is an integer from 1 to 7;
m is 1 when T is oxygen or sulfur, and 2 when T is nitrogen;
n is 2 or 3; and
w is 0 or 1,
with the proviso that each T in structure (I) cannot equal oxygen.

The invention also provides hydrocarbon compositions including at least one protected functionalized initiator, which can also be useful for incorporating a protected carbonyl or carboxyl functionality into a polymer structure, as well as processes for making the initiators of the invention. The initiators are represented by the following structures:

$$M\!-\!(Q)_v\!-\!Z\!-\!\underset{\underset{R_w}{|}}{C}\!-\![T\!-\!(A\!-\!R_1R_2R_3)_m]_n \quad \text{or}$$

(III)

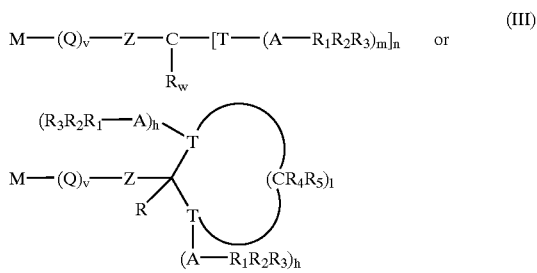

wherein:
each M is independently an alkali metal, preferably selected from the group consisting of lithium, sodium, and potassium;
each Z is independently a branched or straight chain hydrocarbon connecting group which contains 3–25 carbon atoms, optionally substituted with aryl or substituted aryl;

each Q is independently a saturated or unsaturated hydrocarbyl group derived by incorporation of one or more compounds selected from the group consisting of conjugated diene hydrocarbons, alkenylsubstituted aromatic compounds, and mixtures thereof into the M-Z linkage;

each v independently ranges from 0 to 5;

each T is independently selected from the group consisting of oxygen, sulfur, nitrogen, and mixtures thereof;

(A—$R_1R_2R_3$) is a protecting group, in which each A is independently an element selected from Group IVa of the Periodic Table of the Elements; and $R_1$, $R_2$, and $R_3$ are each independently selected from the group consisting of hydrogen, alkyl, substituted alkyl aryl, substituted aryl, cycloalkyl, and substituted cycloalkyl;

R, $R_4$, and $R_5$ are each independently selected from the group consisting of hydrogen, alkyl, substituted alkyl, aryl, substituted aryl, cycloalkyl, and substituted cycloalkyl;

h is 0 when T is oxygen or sulfur, and 1 when T is nitrogen;

l is an integer from 1 to 7;

m is 1 when T is oxygen or sulfur, and 2 when T is nitrogen;

n is 2 or 3; and w is 0 or 1.

Compounds (III) and (IV) efficiently polymerize conjugated diene hydrocarbons, alkenylsubstituted aromatic compounds, and mixtures thereof to afford living polymer anions. The resultant polymer anions, functionalized with a protected functional group at the head, can be quenched to afford a mono-functional polymer; reacted with functionalizing agents to form homo- or hetero-telechelic polymers; or coupled to form telechelic or functionalized radial polymers.

The present invention also provides polymers produced using the electrophiles and/or initiators above, as well as process for making such polymers. In this embodiment of the invention, each T of structure (I) may be oxygen.

Such polymers are useful materials in their own right. For example, polymers derived from electrophiles (I) or (II) and/or initiators (III) or (IV), in which T is N, can be useful in the production of tires with low hysteresis. In addition, the polymers derived from electrophiles (I) or (II) and/or initiators (III) or (IV) can be optionally deprotected, either before or after optional hydrogenation, to afford polymers with carboxyl, aldehyde or ketone end groups. These end groups can enter into subsequent copolymerization reactions to form copolymers. Alternatively, the deprotection and copolymerization can be conducted in the same step to afford the copolymer directly.

DETAILED DESCRIPTION OF THE INVENTION

As used herein, the term "alkyl" refers to straight chain and branched C1–C25 alkyl. The term "substituted alkyl" refers to C1–C25 alkyl substituted with one or more lower C1–C10 alkyl, lower alkylthio, or lower dialkylamino. The term "cycloalkyl" refers to C5–C12 cycloalkyl. The term "substituted cycloalkyl" refers to C5–C12 cycloalkyl substituted with one or more lower C1–C10 alkyl, lower alkylthio, or lower dialkylamino. The term "aryl" refers to C5–C25 aryl having one or more aromatic rings, each of 5 or 6 carbon atoms. Multiple aryl rings may be fused, as in naphthyl or unfused, as in biphenyl. The term "substituted aryl" refers to C5–C25 aryl substituted with one or more lower C1–C10 alkyl, lower alkylthio, or lower dialkylamino. Exemplary aryl and substituted aryl groups include, for example, phenyl, benzyl, and the like.

Novel Electrophiles

The electrophiles of the invention of formula (I) and (II) above can be prepared by standard literature procedures. For example, triethyl ortho-3-chloropropionate can be prepared from 3-chloroprionitrile by the method of G. Casy, J. W. Patterson, and R. J. K. Taylor, *Org. Syn. Coll.* Vol. 8, 415 (1993). Substituted dimethyl or diethyl dithio acetals and ketals can be prepared from the corresponding halo aldehydes or halo ketones and methylthiol or ethylthiol and HCl catalyst, as described by H. Zinner, *Chem. Ber.,* 83, 275 (1980). Halo substituted 1,3-dithianes can be synthesized from the corresponding halo carbonyl compound, 1,3-propanedithiol, and boron trifluoride etherate catalyst, as detailed by J. A. Marshall and J. L. Belletire, *Tetrahedron Letters,* 871 (1971). Analogously, halo substituted 1,3-dithiolanes can be synthesized from the corresponding halo carbonyl compound, 1,3-ethanedithiol, and boron trifluoride etherate catalyst, as detailed by R. P. Hatch, J. Shringarpure, and S. M. Weinreb, *J. Org. Chem.,* 43, 4172 (1978). Substituted dimethyl or diethyl acetals and ketals can be prepared from the corresponding halo aldehydes or halo ketones and methanol or ethanol and anhydrous HCl catalyst, as described by A. F. B. Cameron, J. S. Hunt, J. F. Oughton, P. A. Wilkinson, and B. M. Wilson, *J. Chem. Soc.,* 3864 (1953). The method of R. A. Daignault and E. L. Eliel, *Org. Syn. Col.* Vol. V, 303, (1973), which involves the reaction of a halo-substituted aldehyde or ketone with ethylene glycol, with paratolunesulfonic acid catalyst and azeotropic removal of water, can be employed to prepare the corresponding halo-substituted 1,3-dioxolane. Halo-substituted 1,3-dioxanes can be prepared from the corresponding halo aldehyde or ketone, 1,3-propanediol, paratoluenesulfonic acid catalyst, with azeotropic removal of water, see J. E. Cole, W. S. Johnson, P. A. Robins, and J. Walker, *J. Chem. Soc.,* 244 (1962), and H. Okawara, H. Nakai, and M. Ohno, *Tetrahedron Letters,* 23, 1087 (1982). The reaction of 2-mercaptoethanol with a halo-substituted aldehyde or ketone, with zinc chloride catalyst affords the commensurate substituted 1,3-oxathiolane, as reported by J. Romo, G. Rosenkranz, and C. Djerassi, *J. Amer. Chem. Soc.,* 73, 4961 (1951) and V. K. Yadav and A. G. Fallis, *Tetrahedron Letters,* 29, 897 (1988). Substituted oxazolidines can be synthesized from the corresponding aminoalcohol and a halo-substituted aldehyde or ketone, see E. P. Goldberg and H. R. Nace, *J. Amer. Chem. Soc.,* 77, 359 (1955). In a similar fashion, the method of A. J. Carpenter and D. J. Chadwick, *Tetrahedron,* 41, 3803 (1985) can be employed to generate N,N=-dimethylimidazolidines from a halo aldehyde or ketone and N,N=-dimethyl-1,2-ethylenediamine. Higher homologs can be prepared from the parent halo-substituted imidazolidine via dialkylation, see J. C. Craig and R. J. Young, *Org. Syn. Coll.* Vol. V, 88 (1973).

Novel Initiators

The anionic initiators of the formulae (III) and (IV) are prepared by reacting a compound of the formulae (V) or (VI)

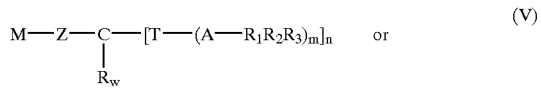

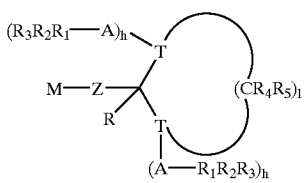

(VI)

wherein M, Z, T, A, R, $R_1$, $R_2$, $R_3$, $R_4$, $R_5$, h, l, m, n and w have the meanings ascribed above, with one or more conjugated diene hydrocarbons, one or more alkenyl substituted aromatic compounds, or mixtures of one or more dienes with one or more alkenylsubstituted aromatic compounds, to form an extended hydrocarbon chain between M and Z in formula (V) and (VI), as well as mixtures thereof with compounds of Formulae (V) and/or (VI). The extended chain is denoted as $Q_v$ in formula (III) and (IV). The initiators can include at least one, and up to five, equivalents of the chain extension agent. The initiators are not so limited, however, and can also include a chain extension formed by incorporation of less than 1 molar equivalent of a chain extension agent.

The compounds of formulae (V) and (VI) are prepared by first reacting a precursor selected from compounds (I) and (II) (which in this aspect of the invention each T of formula I can be oxygen) with an alkali metal in an inert solvent, preferably a predominantly alkane, cycloalkane, or aromatic reaction solvent containing 5 to 10 carbon atoms, or a mixture of such solvents, at a temperature between about 35° C. and about 130° C., to form a protected monofunctional lithium initiator (of formulae (V) and (VI)).

Suitable conjugated diene hydrocarbons include without limitation 1,3-butadiene, isoprene, 2,3-dimethyl-1,3-butadiene, 1,3-pentadiene, myrcene, 2-methyl-3-ethyl-1,3-butadiene, 2-methyl-3-ethyl-1,3-pentadiene, 1,3-hexadiene, 2-methyl-1,3-hexadiene, 3-methyl-1,3-pentadiene, 2,5-dimethyl-2,4-hexadiene, 1,3-heptadiene, 3-methyl-1,3-heptadiene, 1,3-octadiene, 3-butyl-1,3-octadiene, 3,4-dimethyl-1,3-hexadiene, 3-n-propyl-1,3-pentadiene, 4,5-diethyl-1,3-octadiene, 2,4-diethyl-1,3-butadiene, 2,3-di-n-propyl-1,3-butadiene, 2-methyl-3-isopropyl-1,3-butadiene, and the like and mixtures thereof. Among the dialkylbutadienes, it is preferred that the alkyl groups contain from 1 to 3 carbon atoms. Numerous other olefinic monomers are disclosed, for instance, in U.S. Pat. No. 3,377,404.

Suitable alkenylsubstituted aromatic compounds include without limitation styrene, alpha-methylstyrene, vinyltoluene, 2-vinylpyridine, 4-vinylpyridine, 1-vinylnaphthalene, 2-vinylnaphthalene, 1-alpha-methylvinylnaphthalene, 2-alpha-methylvinylnaphathalene, 1,2-diphenyl-4-methylhexene-1 and the like and mixtures of these, as well as alkyl, cycloalkyl, aryl, alkaryl and aralkyl derivatives thereof in which the total number of carbon atoms in the combined hydrocarbon constituents is generally not greater than 18. Examples of these latter compounds include without limitation 3-methylstyrene, 3,5-diethylstyrene, 4-(tert-butyl)-styrene, 2-ethyl-4-benzylstyrene, 4-phenylstyrene, 4-p-tolylstyrene, 2,4-divinyltoluene, 4,5-dimethyl-1-vinylnaphthalene, and the like and mixtures thereof. Again, reference is made to U.S. Pat. No. 3,377,404 for disclosures of additional vinyl-substituted aromatic compounds. Non-polymerizable alkenyl substituted aromatic compounds such as 1,1-diphenylethylene may also be used.

One example of compounds of the general structure (V) is reported in the literature. See B. C. Bennett and R. J. K. Taylor, *Synlett,* 1990, page 601. However, the compound was generated at low temperature (-78° C.) in diethyl ether, and used directly in a synthetic procedure. Compounds of the type (V) and (VI) have not been previously prepared in hydrocarbon solution, or used as protected, functionalized initiators in anionic polymerizations.

Process to Prepare Initiators

Another embodiment of this invention involves the process for the preparation of novel, protected functionalized initiators of formulae (III) and (IV) by metal-halogen exchange reaction of precursor compounds (I) and (II) with an alkali metal in an inert, hydrocarbon solvent. This exchange reaction affords compounds of formulae (V) and (VI), which can then be optionally reacted with one or more conjugated diene hydrocarbons, one or more alkenylsubstituted aromatic compounds, or mixtures of one or more dienes with one or more alkenylsubstituted aromatic compounds to afford the chain extended initiators (III) and (IV).

Incorporation of Q groups into the M-Z linkage to form the compounds of formulae (III) and (IV) above involves addition of compounds of the formulae (V) and (VI), where the symbols have the meanings ascribed above, across the carbon to carbon double bonds in compounds selected from the group consisting of one or more conjugated diene hydrocarbons, one or more alkenylsubstituted aromatic compounds, or mixtures of one or more dienes with one or more alkenylsubstituted aromatic compounds to produce new carbon-lithium bonds of an allylic or benzylic nature, much like those found in a propagating polyalkadiene or polyarylethylene polymer chain derived by anionic initiation of the polymerization of conjugated dienes or arylethylenes. As noted above, the initiators can include at least one, and up to five, equivalents of the chain extension agent. The initiators are not so limited, however, and can also include a chain extension formed by incorporation of less than 1 molar equivalent of a chain extension agent. These new carbon-lithium bonds are now "activated" toward polymerization and so are much more efficient in promoting polymerization than the precursor M-Z (M=Li) bonds, themselves.

Novel Polymers

In another embodiment of the present invention, novel polymer structures are provided. These novel polymers are prepared from the initiators (III) and (IV) above. These novel polymers have unique molecular architecture. The polymers may have mono-functionality, homotelechelic functionality, heterotelechelic functionality, or functionalized radial structure. These novel polymers have the following formulae:

$$FG-[(Q)_x-Z-\underset{R_w}{\underset{|}{C}}-[T-(A-R_1R_2R_3)_m]_n]_y \text{ or}$$

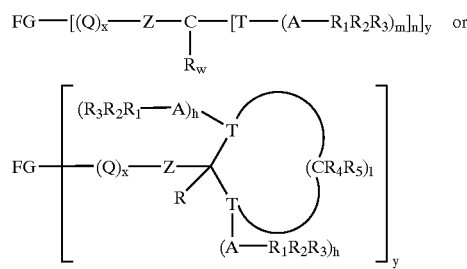

wherein:
each FG is independently hydrogen, a protected functional group, a non-protected functional group, a residue of a difunctional coupling agent or a residue of a multifunctional coupling agent, with the proviso that when each T is oxygen, then FG is not hydrogen;

each Q is independently a saturated or unsaturated hydrocarbyl group derived by incorporation of one or more conjugated diene hydrocarbons, one or more alkenyl-substituted aromatic compounds, or mixtures of one or more conjugated diene hydrocarbons with one or more alkenylsubstituted aromatic compounds;

each x is independently the number of units of conjugated diene hydrocarbon, alkenylsubstituted aromatic compound, or mixture thereof (including that employed originally to solubilize the initiator) and may vary from 10 to 2000;

each Z is independently a branched or straight chain hydrocarbon connecting group which contains 3–25 carbon atoms, optionally substituted with aryl or substituted aryl;

each T is independently selected from the group consisting of oxygen, sulfur, nitrogen, and mixtures thereof;

(A—$R_1R_2R_3$) is a protecting group, in which each A is independently an element selected from Group IVa of the Periodic Table of the Elements; and $R_1$, $R_2$, and $R_3$ are independently selected from the group consisting of hydrogen, alkyl, substituted alkyl, aryl, substituted aryl, cycloalkyl, and substituted cycloalkyl;

R, $R_4$, and $R_5$ are independently selected from the group consisting of hydrogen, alkyl, substituted alkyl, aryl, substituted aryl, cycloalkyl, and substituted cycloalkyl;

h is 0 when T is oxygen or sulfur, and 1 when T is nitrogen;

l is an integer from 1 to 7;

m is 1 when T is oxygen or sulfur, and 2 when T is nitrogen;

n is 2 or 3;

w is 0 or 1; and each y is independently 1 to 30.

Processes for Preparing Novel Polymers

The present invention also provides processes for the anionic polymerization of olefinic-containing monomers. Generally the processes of the invention can be described as follows.

Polymerization of one or more conjugated diene hydrocarbons, one or more alkenylsubstituted aromatic compounds, or a mixture of one or more conjugated diene hydrocarbons with one or more alkenylsubstituted compounds is initiated in a hydrocarbon or mixed hydrocarbon-polar solvent medium at a temperature of 10° C. to 150° C. with one or more initiators having the formula:

$$M-(Q)_v-Z-\underset{R_w}{C}-[T-(A-R_1R_2R_3)_m]_n \quad \text{or} \quad (III)$$

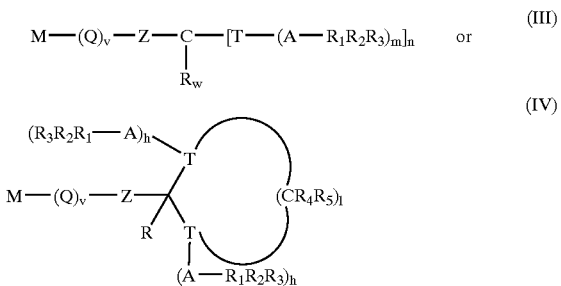

(IV)

wherein M, Z, Q, v, T, A, $R_1$, $R_2$, $R_3$, R, $R_4$, $R_5$, h, l, m, n, and w are the same as defined above, to form an intermediate living polymer anion.

The intermediate polymer anion can be reacted with a reactive compound as known in the art, such as but not limited to ethylene oxide, oxygen, sulfur, carbon dioxide, omega-alkenylarylhalosilanes such as styrenyldimethyl chlorosilane, chlorosilanes such as silicon tetrachloride and dimethyl dichlorosilane, and chlorostannanes such as tin tetrachloride and dibutyltin dichloride, oxetane, silicon acetals, 1,5-diazabicyclo[3.1.0]hexane, N-benzylidene trimethylsilylamide, 1,3-propanesultone, dimethylformamide, allyl bromide, allyl chloride, protected functionalized electrophiles such as compounds of formulas (I) and (II) above, and those described in pending U.S. Pat. Nos. 5,965,681 and 5,910,547, methacryloyl chloride and epichlorohydrin, isomeric divinylbenzenes, diisopropenylbenzene and other materials known in the art to be useful for terminating, end capping or coupling of polymers. The living polymer anion can also be terminated using a suitable protonating agent as known in the art.

The resultant linear or branched polymer is recovered and has one or more terminal functional groups. The polymers can be represented by the formulae $$FG-[(Q)_x-Z-\underset{R_w}{C}-[T-(A-R_1R_2R_3)_m]_n]_y \quad \text{or}$$

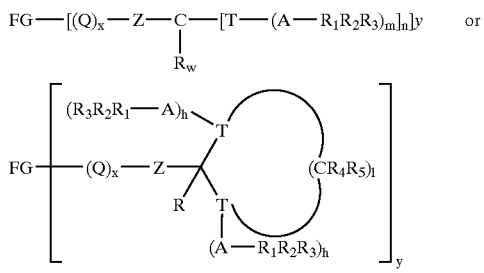

wherein FG, Q, x, A, Z, T, R, $R_1$, $R_2$, $R_3$, $R_4$, $R_5$, $R_6$, h, l, m, n, w and y are defined as above.

The skilled artisan will appreciate that when y is 1, then the resultant polymer is a linear polymer having one protected carbonyl or carboxyl group on one termini of the polymer chain. Also when y is 1, then FG is hydrogen, a protected functional group or a non-protected functional group.

The living polymer can alternatively be reacted with a suitable difunctional coupling agent to couple or link two living polymer anions (which may be the same or different). In this aspect of the invention, y is 2 and FG is the residue of the difunctional coupling agent. When y is 2, the resultant polymer can include protected carbonyl and/or carboxyl groups on opposing termini of the polymer chain, which can have the same or different protecting groups. When y is 2, the polymer can alternatively include a protected carbonyl or protected carboxyl functionality on one end and a non-functional or functional polymer chain having a different protected functionality on the other end. Stated differently the polymer may be homotelechelic, in which the polymer includes terminal protected carbonyl or carboxyl groups that are the same. The polymer may also be heterotelechelic, in which the polymer includes protected carbonyl groups(s) and/or protected carboxyl groups(s) and/or a non-functional group and/or a polymer chain which includes a functional group different from the protected carbonyl and/or carboxyl group at opposing ends that are different from one another.

Still further, the living polymer anions, which may be the same or different, can be coupled using a multifunctional linking agent as known in the art to produce a radial or branched polymer structure in which y is three or greater. In this aspect, FG is the residue of a multifunctional coupling agent. Again, the protected carbonyl and/or carboxyl functionalities can be the same or different in the branched polymers. Also the multi-branched polymer can include polymer chains having non-functional ends and/or polymer chains with a protected functionality that is different from the protected carbonyl or carboxyl group.

The polymer can optionally be reacted with one or more monomers in the presence of a strong acid catalyst to simultaneously deprotect one or more of the functional groups of the polymer and polymerize the liberated functional ends(s) thereof to produce novel segmented block polymers. Exemplary monomers include without limitation cyclic ethers, diamines, diisocyanates, polyisocyanates, di-, poly- and cyclic amides, di- and polycarboxylic acids, diols, polyols, anhydrides, and the like and mixtures thereof.

For example, functionalized polymers can be further reacted with monofunctional monomers, such as caprolactam, or other lactams, to form a polyamide block polymer segment, or cyclic ethers such ethylene oxide to form polyether blocks; or with difunctional monomers, such as diacids or anhydrides and diamines to form polyamide blocks, or diacids or anhydrides and diols to form polyester blocks, or diols and polyols with diisocyanates or polyisocyanates to form polyurethane blocks. Polyisocyanates or polyfunctional polyols are further examples of polyfunctional monomers. The functional group may also contain a reactive olefinic bond, such as a styrenic or acrylic functionality, which will act as a "macromonomer" capable of polymerizing with other free radically polymerizable monomers.

The carbonyl functional groups of the polymers can also be reacted with one or more suitable monomer(s) to form polymer segments or blocks on the polymer chains. For example, aldehyde and/or ketone functional groups can be reacted with a diamine to provide imine groups. A carboxylic acid functional group can be reacted with a diamine to form an amide block. As another example the carboxylic acid functional group can be reacted with a polyol to form a polyester block.

For those polymers which include non-protected functional groups (such as that resulting from the incorporation of ethylene oxide into the living polymer end) the functional polymer can be reacted with one or more monomers in the absence of a strong acid catalyst to yield block copolymers, while maintaining the integrity of at least one of the protective groups. Optionally thereafter additional protective group(s) can be removed and additional liberated functional group(s) reacted with appropriate monomer(s) as described above, which can be the same or different, to produce novel segmented block polymers.

Still further, as discussed in more detail below, polymers having different protecting groups can be treated so as to selectively remove one but not all of the protecting groups, and the liberated functional group reacted with a suitable monomer(s). The remaining protecting groups can optionally thereafter be removed and the thus liberated functional groups also reacted with the same or different monomer(s).

Various techniques as known in the art can be used to remove the protecting group(s), either prior to or after the optional hydrogenation of the residual aliphatic unsaturation. For example, to remove tert-alkyl-protected groups, the protected polymer is mixed with an acidic material, for example, an acidic ion exchange resin such as Amberlyst 15 and heated at an elevated temperature, for example 150° C., until deprotection is complete. In addition, tert-alkyl-protected groups can also be removed by reaction of the polymer with trifluoroacetic acid, or trimethylsilyliodide. Additional methods of deprotection of the tert-alkyl protecting groups can be found in T. W. Greene and P. G. M. Wuts, Protective Groups in Organic Synthesis, Second Edition, Wiley, New York, 1991, page 41. The tert-butyldimethylsilyl protecting groups can be removed by treatment of the polymer with acid, such as hydrochloric acid, acetic acid, paratoluensulfonic acid, or Dowex® 50W-X8. Alternatively, a source of fluoride ions, for instance tetra-n-butylammonium fluoride, potassium fluoride and 18-crown-6, or pyridine-hydrofluoric acid complex, can be employed for deprotection of the tert-butyldimethylsilyl protecting groups. Additional methods of deprotection of the tert-butyldimethylsilyl protecting groups can be found in T. W. Greene and P. G. M. Wuts, Protective Groups in Organic Synthesis, Second Edition, Wiley, New York, 1991, pages 80–83. See also U.S. Pat. No. 5,922,810, issued Date Jul. 13, 1999.

Various techniques as known in the art can also be used to remove the protecting groups from the carbonyl groups as well. See, for example, T. W. Greene and P. G. M. Wuts, Protective Groups in Organic Synthesis, Second Edition, Wiley, New York, 1991, referenced above, for a discussion of various techniques for liberating protected aldehyde, ketone and carboxylic acid groups.

Optionally the polymer is hydrogenated. The polymer can be hydrogenated before or after deprotection and/or other optional downstream reactions such as described in more detail above.

Examples of methods to hydrogenate the polymers of this invention are described in U.S. Pat. Nos. 4,970,254, 5,166,277, 5,393,843 and 5,496,898. The hydrogenation of the functionalized polymer is conducted in situ, or in a suitable solvent, such as hexane, cyclohexane, or heptane. This solution is contacted with hydrogen gas in the presence of a catalyst, such as a nickel catalyst. The hydrogenation is typically performed at temperatures from 25° C. to 150° C. with a archetypal hydrogen pressure of 15 psig to 1000 psig. The progress of this hydrogenation can be monitored by InfraRed (IR) spectroscopy or Nuclear Magnetic Resonance (NMR) spectroscopy. The hydrogenation reaction is conducted until at least 90% of the aliphatic unsaturation has been saturated. The hydrogenated functional polymer is then recovered by conventional procedures, such as removal of the catalyst with aqueous acid wash, followed by solvent removal or precipitation of the polymer.

The inert solvent is preferably a non-polar solvent such as a hydrocarbon, since anionic polymerization in the presence of such non-polar solvents is known to produce polyenes with high 1,4-contents from 1,3-dienes. Solvents useful in practicing this invention include but are not limited to inert liquid alkanes, cycloalkanes and aryl solvents, and mixtures thereof. Exemplary alkanes and cycloalkanes include those containing five to 10 carbon atoms, such as pentane, hexane, cyclohexane, methylcyclohexane, heptane, methylcycloheptane, octane, decane and the like and mixtures thereof. Exemplary aryl solvents include those containing six to ten carbon atoms, such as toluene, ethylbenzene, p-xylene, m-xylene, o-xylene, n-propylbenzene, isopropylbenzene, n-butylbenzene, and the like and mixtures thereof.

Polar modifiers can be added to the polymerization reaction to alter the microstructure of the resulting polymer, i.e., increase the proportion of 1,2 (vinyl) microstructure or to promote functionalization or randomization. Examples of polar modifiers include, but are not limited to, diethyl ether, dibutyl ether, tetrahydrofuran, 2-methyltetrahydrofuran, methyl tert-butyl ether, diazabicyclo[2.2.2]octane, triethylamine, tributylamine, tetramethylenthylene diamine (TMEDA), 1,2-dimethoxyethane (glyme), and the like and mixtures thereof. The amount of the polar modifier added depends on the vinyl content desired, the nature of the monomer, the temperature of the polymerization, and the identity of the polar modifier.

Exemplary olefinic monomers to be anionically polymerized include conjugated diene hydrocarbons, alkenylsubstituted aromatic compounds, and mixtures thereof. The conjugated diene hydrocarbons and alkenylsubstituted aromatic compounds are chosen from the group of unsaturated organic compounds that can be polymerized anionically (i.e. in a reaction initiated by an organo-alkali metal).

Suitable conjugated dienes preferably contain from 4 to 12, more preferably from 4 to 8, carbon atoms per molecule. Examples of these compounds include without limitation 1,3-butadiene, isoprene, 2,3-dimethyl-1,3-butadiene, 1,3-pentadiene, myrcene, 2-methyl-3-ethyl-1,3-butadiene, 2-methyl-3-ethyl-1,3-pentadiene, 1,3-hexadiene, 2-methyl-1,3-hexadiene, 1,3-heptadiene, 3-methyl-1,3-heptadiene, 1,3-octadiene, 3-butyl-1,3-octadiene, 3,4-dimethyl-1,3-hexadiene, 3-n-propyl-1,3-pentadiene, 4,5-diethyl-1,3-octadiene, 2,4-diethyl-1,3-butadiene, 2,3-di-n-propyl-1,3-butadiene, 2-methyl-3-isopropyl-1,3-butadiene, and the like and mixtures thereof. Among the dialkylbutadienes, it is preferred that the alkyl groups contain from 1 to 3 carbon atoms. Of the above monomers 1,3-butadiene, isoprene, 2,3-dimethyl-1,3-butadiene and 1,3-pentadiene are preferred with 1,3-butadiene being particularly preferred.

Suitable alkenylsubstituted aromatic compounds include the optionally-substituted styrenes and vinylnaphthalenes.

The conjugated dienes and alkenylsubstituted aromatic compounds may be polymerized singly, in admixture to form random copolymers, or by charging the compounds to the reaction mixture sequentially to form block copolymers.

Homotelechelic Polymers

Telechelic polymers have found utility in making adhesives, sealants, coatings, films and fibers. These polymers have typically been prepared from a dilithium initiator. See, for example, U.S. Pat. Nos. 5,393,843 and 5,405,911. For example, reaction of 2 equivalents of an alkyllithium reagent, such as sec-butyllithium, with a compound having at least two independently polymerized vinyl groups, such as isomeric divinylbenzenes or isomeric diisopropenylbenzenes, generates a dilithium initiator. Addition of an anionically polymerizable monomer, such as 1,3-butadiene, isoprene, or styrene, affords a polymer chain, with living anions on each of the two termini. This dianion can then be quenched with various functionalizing agents, such as ethylene oxide or carbon dioxide, to afford a telechelic polymer. However, these functionalization reactions are often inefficient, due to the formation of physical gelation phenomena that produce severe mixing problems. See L. Weber, Makromol. Chem., Macromol. Symp., 3, 317 (1986) and U.S. Pat. Nos. 5,393,843 and 5,478,899.

Another embodiment of this invention provides novel protected homotelechelic polymers prepared from protected functionalized electrophiles (I) and (II) (which in this aspect of the invention, each T of formula I can be oxygen). In addition, these novel polymers can be optionally hydrogenated, either before or after the optional removal of the protecting groups ("deprotection") to afford new polymers. Furthermore, the procedures employed to prepare these novel compounds are unique.

In contrast to telechelic polymers of the prior art, the molecular architecture of compounds of the present invention can be precisely controlled. High functionalization of the living polymer dianions is achieved, as the functionalizing agents of the current invention do not cause gelation to occur, upon their addition to a living polymer. The nature of the functional group, and its protecting group can be varied, simply by changing the functionalizing agent. The process to prepare these novel polymers is also unique, in that efficient functionalization of the living polymer dianions is achieved.

Novel telechelic polymers of the present invention can be prepared as described in detail below.

Two equivalents of a lithium initiator, such as an alkyllithium initiator R-Li, wherein R represents an aliphatic, cycloaliphatic, or aromatic radical, can be added to a compound having at least two independently polymerized vinyl groups, such as 1,3-divinylbenzene or 1,3-diisopropenylbenzene, to afford a dilithium initiator. Such initiators include, but are not limited to, n-butyllithium, sec-butyllithium, tert-butyllithium, 2-ethylhexyllithium, hexyllithium, and the like, and mixtures thereof. One or more conjugated diene hydrocarbons, alkenylsubstituted aromatic compounds, or mixtures thereof, is added to grow living polymer arms from the central core. Two or more equivalents of a functionalizing agent (electrophile) is then added, which have one of the following structures:

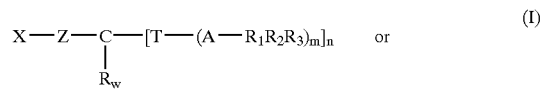

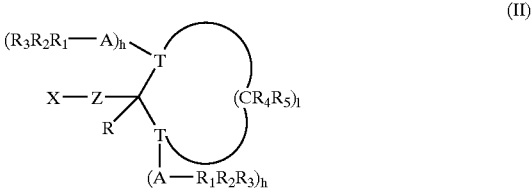

wherein X, Z, T, A, $R_1$, $R_2$, $R_3$, R, $R_4$, $R_5$, h, l, m, n, and w are the same defined above, except that in this aspect of the invention, each T of the compounds of formula I can be oxygen.

This procedure efficiently functionalizes each living anion site of the polymer with a protected functional group. The nature of the protected functional group can be varied by merely changing the identity of the electrophile.

The functionalized multi-arm polymers of the present invention can be defined as

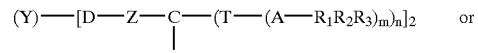

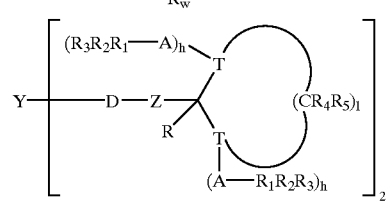

wherein:
  each Y independently represents a core derived by incorporation of a molecule having at least two independently polymerized vinyl groups, such as 1,3-divinylbenzene or 1,4-divinylbenzene;
  each D independently represents a hydrogenated or unsaturated block derived by anionic polymerization of one or more conjugated diene hydrocarbons, for example 1,3-butadiene or isoprene, one or more alkenylsubstituted aromatic compounds, such as styrene or alpha-methylstyrene, or one or more conjugated diene hydrocarbons with one or more alkenylsubstituted aromatic compounds; and Z, T, A, R, $R_1$, $R_2$, $R_3$, $R_4$, $R_5$, h, l, m, n and w are defined as above.

These novel polymers can by optionally hydrogenated to afford other novel polymers. The protecting groups can be removed either prior to or following this hydrogenation. The deprotected polymers are also novel.

After deprotection, the polymer has the following structure:

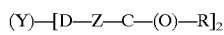

or

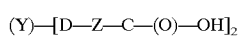

wherein Y, D, and Z are the same as defined above. One advantage of the present invention is the ability to provide a high degree of functionalization. In particular, the homotelechelic polymers produced in accordance with this aspect of the invention can have a high level of functionalization, of up to and greater than 1.9. In contrast, homotelechelic polymers prepared using dilithium technology have a significantly lower degree of functionality.

Advantages of the homotelechelic polymers produced by the present invention include highly efficient functionalization of the living anion sites on the arms of the polymer; various protected functional groups can be introduced; and less expensive than alternative methods to prepare telechelic polymers.

Heterotelechelic Polymers

Polymers prepared from dilithium initiators necessarily have the same functional group on each termini ("homotelechelic"). In yet another aspect of the invention, novel "heterotelechelic" polymers, molecules with different functional groups at each termini, are disclosed. In contrast to telechelic polymers of the prior art, the molecular architecture of compounds of the present invention can be precisely controlled. High functionalization of the living polymer anions is achieved, as the functionalizing agents of the current invention do not cause gelation to occur, upon their addition to a living polymer. The nature of the functional group on each termini, and its protecting group, can be varied simply by changing the functionalized initiator or the functionalizing agent. The process to prepare these novel polymers is also unique, in that efficient functionalization of the living polymer anions is achieved.

Novel, protected, heterotelechelic polymers of the present invention comprise the structures:

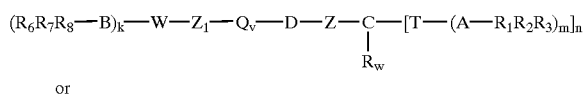

or

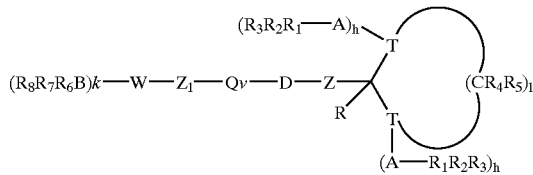

wherein:
each D independently represents a hydrogenated or unsaturated block derived by anionic polymerization of one or more conjugated diene hydrocarbons, for example 1,3-butadiene or isoprene, or one or more alkenylsubstituted aromatic compounds, such as styrene or alpha-methylstyrene, or one or more conjugated diene hydrocarbons with one or more alkenylsubstituted aromatic compounds;

each Z is independently a branched or straight chain hydrocarbon connecting group which contains 1–25 carbon atoms, optionally substituted with aryl or substituted aryl;

each $Z_1$, is independently a branched or straight chain hydrocarbon connecting group which contains 3–25 carbon atoms, optionally substituted with aryl or substituted aryl;

each Q is independently a saturated or unsaturated hydrocarbyl group derived by incorporation of one or more conjugated diene hydrocarbons, one or more alkenyl-substituted aromatic compounds, or mixtures of one or more conjugated diene hydrocarbons with one or more alkenylsubstituted aromatic compounds;

each v independently ranges 0 to 5;

each T and W is independently selected from the group consisting of oxygen, sulfur, nitrogen and mixtures thereof;

(A—$R_1R_2R_3$) and (B—$R_6R_7R_8$) are protecting groups in which A and B are each independently selected from elements selected from Group IVa of the Periodic Table of the Elements; and $R_1$, $R_2$, $R_3$, $R_6$, $R_7$, and $R_8$ are each independently selected from the group consisting of hydrogen, alkyl, substituted alkyl, aryl, substituted aryl, cycloalkyl, and substituted cycloalkyl;

R, $R_4$, and $R_5$ are each independently selected from the group consisting of hydrogen, alkyl, substituted alkyl, aryl, substituted aryl, cycloalkyl, and substituted cycloalkyl;

h is 0 when T is oxygen or sulfur, and 1 when T is nitrogen;

l is an integer from 1 to 7;

k and m are 1 when T or W is oxygen or sulfur, and 2 when T or W is nitrogen;

n is 2 or 3; and w is 0 or 1.

Novel heterotelechelic polymers of the present invention are prepared as described in detail below.

Living polymer anions are prepared by anionically polymerizing one or more conjugated diene hydrocarbons, one or more alkenylsubstituted aromatic compounds or a mixture of one or more conjugated diene hydrocarbons with one or more alkenylsubstituted aromatic compounds, in an inert solvent, at a temperature from −30° C. to 150° C., for a period of at least one hour, with one or more protected functionalized initiators having the formula:

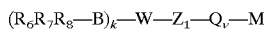 (VII)

or

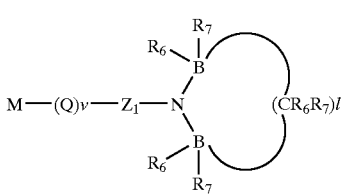
(IX)

wherein:
- each M is independently an alkali metal, preferably selected from the group consisting of lithium, sodium and potassium;
- each Q is independently a saturated or unsaturated hydrocarbyl group derived by incorporation of one or more conjugated diene hydrocarbons, one or more alkenyl-substituted aromatic compounds, or mixtures of one or more conjugated diene hydrocarbons with one or more alkenylsubstituted aromatic compounds into the M-Z linkage;
- each v independently ranges from 0 to 5;
- each $Z_1$ is independently a branched or straight chain hydrocarbon connecting group which contains 3–25 carbon atoms, optionally substituted with aryl or substituted aryl;
- each W is independently selected from the group consisting of oxygen, sulfur, nitrogen and mixtures thereof;
- (B—$R_6R_7R_8$) is a protecting group in which each B is independently an element selected from Group IVa of the Periodic Table of the Elements; and $R_6$, $R_7$, and $R_8$ are each independently selected from the group consisting of hydrogen, alkyl, substituted alkyl, aryl, substituted aryl, cycloalkyl, and substituted cycloalkyl;
- l is an integer from 1 to 7; and
- k is 1 when W is oxygen or sulfur, and 2 when W is nitrogen.

This is followed by addition of an equivalent of a functionalizing agent (electrophile), which has the following structure:

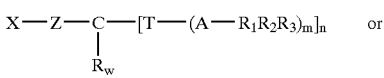
(I)

or

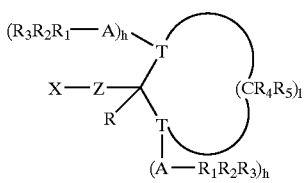
(II)

wherein:
- X, Z, T, A, $R_1$, $R_2$, $R_3$, R, $R_4$, $R_5$, h, l, m, n, and w are the same as defined above, except that in this aspect of the invention each T of the compounds of formula I can be oxygen.

U.S. Pat. Nos. 5,496,940 and 5,527,753 disclose novel, tertiary amino containing initiators which are soluble in hydrocarbon solvents. U.S. Pat. No. 5,600,021 discloses novel monofunctional ether initiators which are soluble in hydrocarbon solvents. U.S. Pat. No. 5,362,699 discloses novel monofunctional silyl ether initiators which are soluble in hydrocarbon solvents. Each of these types of initiators can be employed in the present invention.

The initiators of the formulae

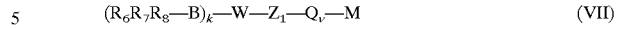
(VII)

or

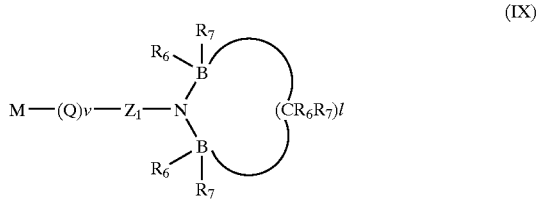
(IX)

are prepared by reacting a compound of the formula

(VIII)

or

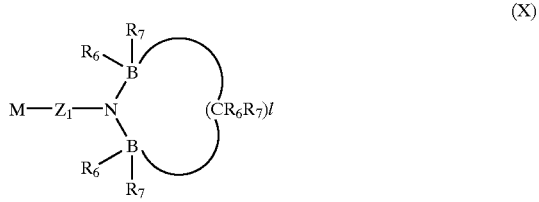
(X)

wherein M, $Z_1$, W, B, $R_6$, $R_7$, $R_8$, k and l have the meanings ascribed above, with one or more conjugated diene hydrocarbons, one or more alkenylsubstituted aromatic compounds, or mixtures of one or more conjugated diene hydrocarbons with one or more alkenylsubstitued aromatic compounds, to form an extended hydrocarbon chain between M and Z in formula (VIII) and (X), which extended chain is denoted as $Q_v$ in formula (VII) and (IX). As noted above, the initiators can include at least one, and up to five, equivalents of the chain extension agent. The initiators are not so limited, however, and can also include a chain extension formed by incorporation of less than 1 molar equivalent of a chain extension agent.

The compounds of formula (VIII) and (X) are prepared by first reacting in an inert solvent a selected tertiary amino-1-haloalkane or an omega-hydroxy-protected-1-haloalkane or an omega-thio-protected-1-haloalkane, depending on whether "W" is to be N, O or S, (the alkyl portions of the haloalkyl groups contain 3 to 25 carbon atoms) with an alkali metal, preferably lithium, at a temperature between about 35° C. and about 130° C., preferably at the solvent reflux temperature, to form a protected monofunctional lithium initiator (of formula (VIII) or (X)) which is then optionally reacted with a one or more conjugated diene hydrocarbons, one or more alkenylsubstituted aromatic compounds, or mixtures of one or more conjugated diene hydrocarbons with one or more alkenylsubstituted aromatic compounds, in a predominantly alkane, cycloalkane, or aromatic reaction solvent, which solvent contains 5 to 10 carbon atoms, and mixtures of such solvents, to produce a monofunctional initiator with an extended hydrocarbon chain or tether between the metal atom (M) and element (W) in formula (VII) and (IX)above and mixtures thereof with compounds of formula (VIII) and (X), respectively.

These novel polymers can by optionally hydrogenated to afford other novel polymers. The protecting groups can be removed either prior to or following this optional hydrogenation of residual aliphatic unsaturation The deprotected polymers are also novel. The hydrogenation and deprotecting techniques as described above can be useful in this aspect of the invention as well.

If the protecting groups on each end of the telechelic polymer can be removed the same deprotection procedure, complete deprotection of the polymer can be achieved in a single step. After complete deprotection, the produced telechelic polymer has the following structure:

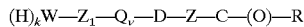

or

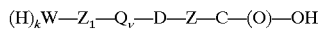

wherein D, Q, Z, $Z_1$, W, R, v, and k are defined as above.

Another aspect of this invention is directed to a process for the preparation of a linear polymer possessing one free telechelically functional group and one protected telechelically functional group. The process comprises selectively deprotecting one type of dissimilarly protected functionality on the end(s) of the arms of the linear polymer chains, produced as described above, using selective reagents specifically suited to remove the targeted protective group, —B—$R_6R_7R_8$, and liberate the desired functionality, —W—$(H)_m$ on the end of the polymer chain. Alternatively, the acetal, ketal, or orthoester group can be selectively deprotected to afford a heterotelechelic polymer with a carbonyl or carboxyl group on one termini of the polymer chain. Such polymers are represented below:

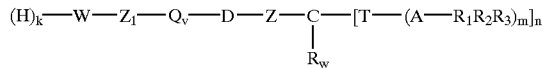

or

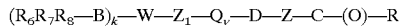

or

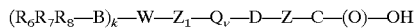

or

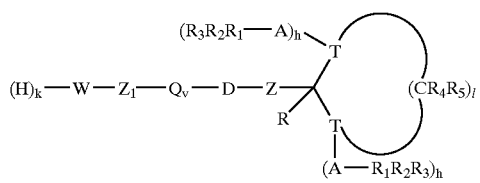

wherein D, A, B, R, $R_1$, $R_2$, $R_3$, $R_4$, $R_5$, $R_6$, $R_7$, $R_8$, Q, Y, Z, $Z_1$, T, W, h, k, l, m, n, v and w are defined as above.

The following table details experimental conditions that will selectively remove one of the protecting groups (more labile) from the polymer, while retaining the other protecting group (more stable).

| LABILE | STABLE | CONDITIONS |
|---|---|---|
| t-Butyldimethylsilyl | Acetal | Tetrabutylammonium fluoride |
| t-Butyldimethylsilyl | Ketal | Tetrabutylammonium fluoride |
| t-Butyldimethylsilyl | Orthoester | Tetrabutylammonium fluoride |
| t-Butyldimethylsilyl | Aminal | Tetrabutylammonium fluoride |
| Acetal | t-Butyl | 1 N HCl |
| Ketal | t-Butyl | 1 N HCl |
| Orthoester | t-Butyl | 1 N HCl |
| Aminal | t-Butyl | 1 N HCl |
| Acetal | Dialkylamino | 1 N HCl |
| Ketal | Dialkylamino | 1 N HCl |
| Orthoester | Dialkylamino | 1 N HCl |
| Aminal | Dialkylamino | 1 N HCl |
| 2,2,5,5-tetramethyl-2,5-disila-1-azacyclopentane | Acetal | Tetrabutylammonium Fluoride |
| 2,2,5,5-Tetramethyl-2,5-disila-1-azacyclopentane | Ketal | Tetrabutylammonium Fluoride |
| 2,2,5,5-Tetramethyl-2,5-disila-1-azacyclopentane | Orthoester | Tetrabutylammonium Fluoride |
| 2,2,5,5-tetramethyl-2,5-disila-1-azacyclopentane | Aminal | Tetrabutylammonium Fluoride |

Advantages of the heterotelechelic polymers produced by the present invention include: highly efficient functionalization of the living anion sites on the arms of the polymer; various heteroatoms can be introduced by changing the nature of the initiator or the electrophile; different protecting groups can be employed to mask the heteroatoms; and the different protecting groups can be selectively removed, if desired, and the newly liberated functional group can be further derivatized or copolymerized by reactions as described in more detail above.

EXAMPLE 1

Preparation of 2-(3-Chloropropyl)-5,5-dimethyl-2-methyl-1,3-dioxane

A one liter, round bottom flask is equipped with a magnetic stir bar, a Dean-Stark water separator, a reflux condenser and a nitrogen inlet. This apparatus is dried in an oven overnight at 120° C., assembled hot, and is allowed to cool to room temperature in a stream of nitrogen. The flask is charged with 144.70 grams (1.20 moles) of 5-chloro-2-pentanone, 185.00 grams (1.32 moles) of 2,2-dimethyl-1,3-propandiol, 300 ml of toluene and 0.05 grams of p-toluenesulfonic acid catalyst. The flask is placed in a heating mantle and the reaction mixture is heated to reflux until close to the theoretical amount of water (21.6 ml) is collected in the Dean-Stark trap. The reaction mixture is allowed to cool to room temperature, transferred to a separatory funel and washed with 200 ml portions of saturated sodium bicarbonate solution, and three times with water. The resulting organic layer is separated, dried over anhydrous potassium carbonate, filtered, and concentrated under reduced pressure on a rotary evaporator. This affords a clear, pale yellow oil, which is employed in the subsequent reactions without further purification.

Yield=231.77 grams (93.5%).

EXAMPLE 2

Preparation of 3,3,3-Trimethoxy-1-propyllithium

A 500-milliliter, three-necked, Morton flask is fitted with a mechanical stirrer, a 125 milliliter pressure-equalizing addition funel, and a Claisen adapter equipped with a thermocouple and a dry ice condenser with an argon inlet. This apparatus is dried in an oven overnight at 125° C., assembled hot, and is allowed to cool to room temperature in a stream of argon. Lithium metal dispersion, 1.1% sodium, is washed free of mineral oil with hexane (3×100 milliliters) and pentane (1×100 milliliters). The resultant lithium metal is dried in a stream of argon, weighed (7.00 grams, 1.01 moles, 2.8 equivalents), and transferred to the reaction flask with 300 milliliters of cyclohexane. The reaction mixture is stirred at 600 RPM's and heated to 60° C. with a heat gun. The heat source is removed. 3,3,3-Trimethoxy-1-chloropropane, 60.70 grams (0.360 moles, 1.00 equivalent) is added dropwise via the addition funel. This precursor is prepared from 3-chloropropionitrile by the method described by G. Casy, J. W. Patterson, and R. J. K. Taylor, *Org. Syn. Coll.* Vol. 8, 415 (1993). An exotherm is detected after 10% of the halide feed has been added. A dry ice/hexane cooling bath is applied as needed to maintain the reaction temperature between 60–65° C. The total halide feed time is sixty minutes. The reaction temperature falls off rapidly to room temperature at the conclusion of the feed. The reaction mixture is stirred for two hours at room temperature, then the reaction mixture is transferred with argon pressure to a dry, sintered glass pressure filter. The product solution is pressure filtered with 3 psi argon. The lithium chloride muds are reslurried with fresh cyclohexane (2×50 milliliters). The filtrate is a clear, light yellow solution, yield=352.5 grams.

Total Base=3.6 wt. %.

Active C-Li=3.5 wt. %.

Yield=24.5% (based on active analysis).

A one milliliter aliquot of this solution is withdrawn, cooled to 0° C., and carefully quenched with water. The organic layer is then analyzed by gas chromatography. A Perkin Elmer Autosystem CC, equipped with a 30 meter, 0.53 mm AT-1 column, is employed for this analysis. All the 3,3,3-trimethoxy-1-chloropropane has been consumed, with the formation of a single, lower boiling compound, identified as 1,1,1-trimethoxypropane by GC/MS.

EXAMPLE 3

Preparation of 3,3,3-Trimethoxy-1-propyllithium Chain Extended With Isoprene

A 500-milliliter, three-necked, Morton flask is fitted with a mechanical stirrer, a 125 milliliter pressure-equalizing addition funel, and a Claisen adapter equipped with a thermocouple and a dry ice condenser with an argon inlet. This apparatus is dried in an oven overnight at 125° C., assembled hot, and allowed to cool to room temperature in a stream of argon. Lithium metal dispersion, 1.1% sodium, is washed free of mineral oil with hexane (3×100 milliliters) and pentane (1×100 milliliters). The resultant lithium metal is dried in a stream of argon, weighed (6.25 grams, 0.900 moles, 2.80 equivalents), and transferred to the reaction flask with 220 milliliters of cyclohexane. The reaction mixture is stirred at 600 RPM's and heated to 60° C. with a heat gun. The heat source is removed. 3,3,3-Trimethoxy-1-chloropropane, 54.19 grams (0.322 moles, 1.00 equivalent) is added dropwise via the addition funel. This precursor is prepared from 3-chloropropionitrile by the method described by G. Casy, J. W. Patterson, and R. J. K. Taylor, *Org. Syn. Coll.* Vol. 8, 415 (1993). An exotherm is detected after 10% of the halide feed has been added. A dry ice/hexane cooling bath is applied as needed to maintain the reaction temperature between 60–65° C. The total halide feed time is sixty-four minutes. The reaction temperature falls off rapidly to room temperature at the conclusion of the halide feed. The reaction is stirred at room temperature for two hours. The reaction mixture is reheated to 60° C. with a heat gun then the heat is removed. Isoprene (43.81 grams, 0.643 moles, 2.00 equivalents) is added dropwise via the addition funel. An exotherm is detected after 30% of the feed has been added. A dry ice/hexane cooling bath is applied as needed to maintain the reaction temperature between 60–65° C. The total isoprene feed time is thirty-five minutes. The temperature falls off rapidly to room temperature. The reaction mixture is stirred at room temperature for two hours, then is transferred with argon pressure to a dry sintered glass pressure filter. The product solution is pressure filtered with 3 psi argon. The lithium chloride muds are reslurried with fresh cyclohexane (2×30 milliliters). The filtrate is a clear, amber solution, yield=374.22 grams.

Total Base=22.0 wt. %.

Active C-Li=21.1 wt. %.

Yield=88.8% (based on active analysis).

EXAMPLE 4

Preparation of Protected Alpha-Carboxy-Omega-Hydroxy-Polyisoprene

A 500 ml. glass reactor is equipped with three break-seal reagent ampoules, a sampling port attached with a Teflon® stopcock, an inlet tube fitted with a septum cap, and a magnetic stir bar. This reactor is flame sealed to a high vacuum line, and evacuated at 120° C. for 8 hours. The flask is refilled with dry argon, and allowed to cool to room temperature. 3,3,3-Trimethoxy-1-propyllithium chain extended with isoprene, 21.1 wt. % in cyclohexane, 0.82 grams contained (2.97 mmoles) is added to the reactor with a syringe via the inlet tube. Cyclohexane, 300 ml., is then vacuum distilled directly into the reactor. The flask is then removed from the vacuum line by a flame seal. Purified isoprene (12.3 grams) is added by breaking the seal of the ampoule containing isoprene. The polymerization reaction proceeds for eight hours at room temperature. The living polymer is functionalized by the addition of an excess of ethylene oxide, 0.66 grams (15 mmoles, 5 equivalents) added from the second break-seal ampoule. The polymer is then terminated with a large amount of degassed methanol, added from the third break-seal ampoule. The functionalized polymer is recovered by precipitation two times into methanol, and vacuum dried for twenty four hours.

The resultant functionalized polymer is characterized by SEC, and has the following properties:

$M_n$=4.23×10$^3$ g/mole $M_w/M_n$=1.08

Yield=93.0%

TLC analysis using toluene as an eluent shows only one spot with moderate polarity. This indicates that all the polymer is functionalized. The polymer is further characterized by $^1$H NMR which indicates a 1,4 microstructure of 87%, and the presence of the O-Me signals as a sharp singlet at 3.24 ppm.

EXAMPLE 5

Preparation of Alpha-Carboxy-Omega-Hydroxy-Polyisoprene

A 100 ml. flask is fitted with a magnetic stir bar, a reflux condenser, and a nitrogen inlet. This apparatus is dried in an oven overnight at 125° C., assembled hot, and allowed to cool to room temperature in a stream of nitrogen. The protected alpha-carboxy-omega-hydroxypolyisoprene polymer, prepared in Example 4, (2.0 gram) and tetrahydrofuran (20 ml) are added to the flask. This is followed by addition of 5% aqueous hydrochloric acid, until pH=1–2. The reaction mixture is heated to reflux for seven hours. The reaction mixture is allowed to cool to room temperature. After solvent removal and vacuum drying, the resultant polymer is analyzed by SEC, TLC and $^1$H NMR.

$M_n$=4.19×10$^3$ g/mole $M_w/M_n$=1.08

TLC analysis using toluene as an eluent shows only one very polar spot. This indicates that all the polymer is deprotected. The O-Me signal at 3.24 ppm is completely absent in the $^1$H NMR.

EXAMPLE 6

Preparation Of Heterotelechelic Functionalized Polybutadiene

A 500 ml. glass reactor is equipped with three break-seal reagent ampoules, a sampling port attached with a Teflon® stopcock, an inlet tube fitted with a septum cap, and a magnetic stir bar. This reactor is flame sealed to a high vacuum line, and evacuated at 120° C. for 8 hours. The flask is refilled with dry argon, and allowed to cool to room temperature. 3-(1,1-Dimethylethoxy)-1-propyllithium, 20.0 wt. % in cyclohexane, 1.110 grams contained (4.31 mmoles) is added to the reactor with a syringe via the inlet tube. Cyclohexane, 300 ml., is then vacuum distilled directly into the reactor. The flask is then removed from the vacuum line by a flame seal. The reactor flask is then heated to 50° C., and 15.2 grams of purified butadiene is added by breaking the seal of the ampoule containing butadiene. The reaction mixture is held 50–55° C. at for 5 hours. The living polymer of alpha-(t-butoxy)-functionalized-poly(butadienyl)-lithium is functionalized by the addition of 0.27 grams (6.45 mmoles, 1.5 equivalents) of anhydrous lithium chloride (previously dried overnight at 120° C. under vacuum) via the inlet tube and 0.96 grams (6.45 mmoles, 1.5 equivalents) of 2-(3-chloropropyl)-N-methyl-oxazolidine is then added from the second break-seal ampoule. The functionalizing agent, 2-(3-chloropropyl)-N-methyl-oxazolidine, is prepared from 3-chloropropionaldehyde and 2-methylaminoethanol by the procedure of E. P. Goldberg and H. R. Nace, *J. Amer. Chem. Soc.*, 77, 359 (1955). The reaction mixture is stirred for several hours and the progress of the reaction is monitored by TLC. Degassed methanol is then added from the third break-seal ampoule. The alpha, omega-functionalized heterotelechelic polymer is recovered by precipitation two times into methanol, and is vacuum dried for twenty four hours.

The resultant heterotelechelic functionalized polymer is characterized by SEC, and has the following properties:

$M_n$=3.7×10$^3$ g/mole $M_w/M_n$=1.05

Yield=93.0%

By TLC analysis using toluene as an eluent, no unfunctionalized polymer is detected. The polymer is further characterized by $^1$H NMR which indicates a 1,4 microstructure of 85% and exhibits a peak at δ=2.20 ppm assigned to the N-methyl group and at δ=1.17 ppm assigned to the O-t-Butyl group.

The foregoing is illustrative of the present invention and is not to be construed as limiting thereof. Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed is:

1. A polymer of the formula

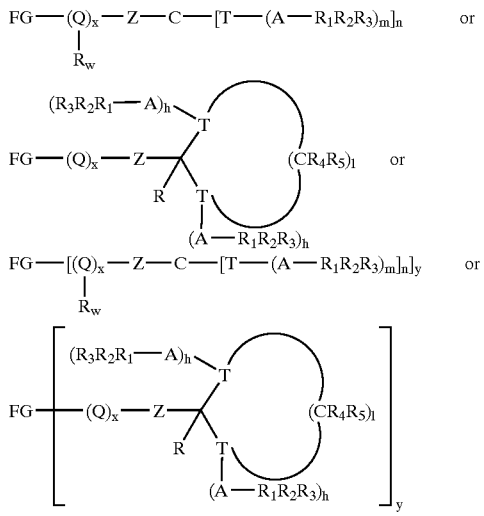

wherein each FG is independently hydrogen, a protected functional group, a non-protected functional group, the residue of a difunctional coupling agent, or the residue of a multifunctional coupling agent, with the proviso that when each T is oxygen, then FG is not hydrogen;

each Q is independently a saturated or unsaturated hydrocarbyl group derived by incorporation of one or more conjugated diene hydrocarbons, one or more alkenyl-substituted aromatic compounds, or mixtures of one or more conjugated diene hydrocarbons with one or more alkenylsubstituted aromatic compounds;

each x is independently the number of units of conjugated diene hydrocarbons, alkenylsubstituted aromatic compounds, or mixture thereof and ranges from about 10 to about 2000;

each Z is independently a branched or straight chain hydrocarbon connecting group which contains 3–25 carbon atoms, optionally substituted with aryl or substituted aryl;

each T is independently selected from the group consisting of oxygen, sulfur, nitrogen, and mixtures thereof;

(A—R$_1$R$_2$R$_3$) is a protecting group, in which each A is independently an element selected from Group IVa of the Periodic Table of the Elements; and R$_1$, R$_2$, and R$_3$ are each independently selected from the group consisting of hydrogen, alkyl, substituted alkyl, aryl, substituted aryl, cycloalkyl, and substituted cycloalkyl;

R, R$_4$, and R$_5$ are each independently selected from the group consisting of hydrogen, alkyl, substituted alkyl, aryl, substituted aryl, cycloalkyl and substituted cycloalkyl;

h is 0 when T is oxygen or sulfur, and 1 when T is nitrogen;

l is an integer from 1 to 7;

m is 1 when T is oxygen or sulfur, and 2 when T is nitrogen;

n is 2 or 3;

w is 0 or 1; and y is 1.

2. The polymer of claim 1, wherein said polymer is a compound of the formula

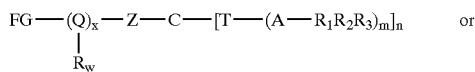

or

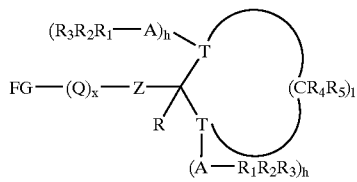

wherein each FG is independently hydrogen, a protected functional group, or a non-protected functional group.

3. The polymer of claim 1, wherein said polymer is a compound of the formula

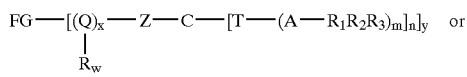

or

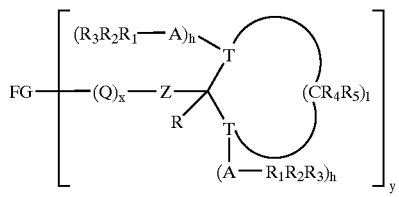

wherein:
each FG is independently the residue of a difunctional coupling agent; and
y is 2.

4. The polymer of claim 3, wherein said polymer is a homotelechelic polymer.

5. The polymer of claim 3, wherein said polymer is a telechelic polymer.

6. The polymer of claim 1, comprising a compound of the structure

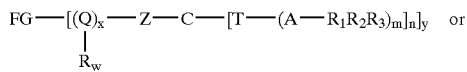

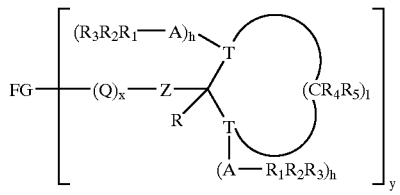

wherein:
each FG is independently the residue of a multifunctional coupling agent; and
y is 3 to 30.

7. A polymer of the formula

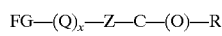

or

wherein
each FG is independently a protected functional group or a non-protected functional group;
each Q is independently a saturated or unsaturated hydrocarbyl group derived by incorporation of one or more conjugated diene hydrocarbons, one or more alkenyl-substituted aromatic compounds, or mixtures of one or more conjugated diene hydrocarbons with one or more alkenylsubstituted aromatic compounds;
each x is independently the number of units of conjugated diene hydrocarbon, alkenylsubstituted aromatic compound, or mixture thereof and ranges from about 10 to about 2000;
each Z is independently a branched or straight chain hydrocarbon connecting group which contains 3–25 carbon atoms, optionally substituted with aryl or substituted aryl; and
each R is independently selected from the group consisting of hydrogen, alkyl, substituted alkyl, aryl, substituted aryl, cycloalkyl and substituted cycloalkyl.

8. A polymer of the formula

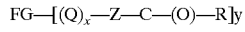

or

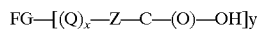

wherein
each FG is independently the residue of a difunctional coupling agent or the residue of a multifunctional coupling agent;
each Q is independently a saturated or unsaturated hydrocarbyl group derived by incorporation of one or more conjugated diene hydrocarbons, one or more alkenyl-substituted aromatic compounds, or mixtures of one or more conjugated diene hydrocarbons with one or more alkenylsubstituted aromatic compounds;
each x is independently the number of units of conjugated diene hydrocarbons, alkenylsubstituted aromatic compounds, or mixture thereof and ranges from about 10 to about 2000;
each Z is independently a branched or straight chain hydrocarbon connecting group which contains 3–25 carbon atoms, optionally substituted with aryl or substituted aryl;
each R is independently selected from the group consisting of hydrogen, alkyl, substituted alkyl, aryl, substituted aryl, cycloalkyl and substituted cycloalkyl; and
each y is independently 2 to 30.

9. The polymer of claim 8, wherein y is 2.

10. The polymer of claim 8, wherein y is 3 to 30.

11. A process for preparing polymers having a protected terminal carbonyl or carboxyl group of the formula

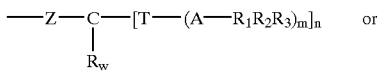

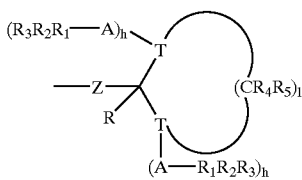

wherein:
  each Z is independently a branched or straight chain hydrocarbon connecting group which contains 3–25 carbon atoms, optionally substituted with aryl or substituted aryl;
  each T is independently selected from the group consisting of oxygen, sulfur, nitrogen, and mixtures thereof;
  (A—$R_1R_2R_3$) is a protecting group, in which each A is independently an element selected from Group IVa of the Periodic Table of the Elements; and $R_1$, $R_2$, and $R_3$ are each independently selected from the group consisting of hydrogen, alkyl, substituted alkyl, aryl, substituted aryl, cycloalkyl, and substituted cycloalkyl;
  R, $R_4$, and $R_5$ are each independently selected from the group consisting of hydrogen, alkyl, substituted alkyl, aryl, substituted aryl, cycloalkyl and substituted cycloalkyl;
  h is 0 when T is oxygen or sulfur, and 1 when T is nitrogen;
  l is an integer from 1 to 7;
  m is 1 when T is oxygen or sulfur, and 2 when T is nitrogen;
  n is 2 or 3; and
  w is 0 or 1,
the process comprising:
  initiating anionic polymerization of one or more conjugated diene hydrocarbons, one or more alkenylsubstituted aromatic compounds, or a mixture of one or more conjugated diene hydrocarbons with one or more alkenylsubstituted aromatic compounds with one or more protected functional initiators of the formula

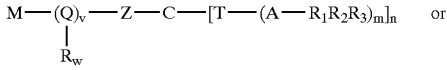

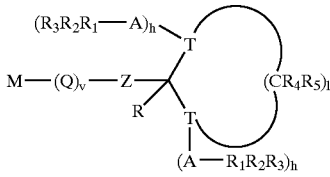

wherein:
  each M is independently an alkali metal;
  each Q is independently a saturated or unsaturated hydrocarbyl group derived by incorporation of one or more compounds selected from the group consisting of conjugated diene hydrocarbons, alkenylsubstituted aromatic compounds, and mixtures thereof;
  each v independently ranges from 0 to 5; and
  Z, T, A, $R_1$, $R_2$, $R_3$, R, $R_4$, $R_5$, h, l, m, n, and w are the same as defined above, to produce one or more living polymer anions; and reacting one or more of said living polymer anions with at least one of a quenching agent, functionalizing reagent, or coupling agent, with the proviso that when each T is oxygen, then the living polymer anions are not reacted with a quenching agent.

12. The process of claim 11, further comprising:
  removing one or more protecting groups to liberate one or more functional groups; and
  reacting said one or more liberated functional groups with one or more monomers to form one or more polymer segments.

13. The process of claim 11, wherein said one or more living polymer anions is reacted with one or more quenching agents to form one or more polymers of the formula

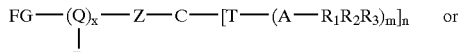

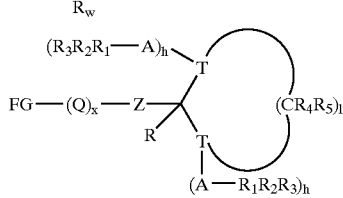

wherein:
  each FG is independently hydrogen;
  each Q is independently a saturated or unsaturated hydrocarbyl group derived by incorporation of one or more conjugated diene hydrocarbons, one or more alkenyl-substituted aromatic compounds, or mixtures of one or more conjugated diene hydrocarbons with one or more alkenylsubstituted aromatic compounds; and
  each x is independently the number of units of conjugated diene hydrocarbons, alkenylsubstituted aromatic compounds, or mixture thereof and ranges from about 10 to about 2000.

14. The process of claim 11, wherein said one or more living polymer anions is reacted with one or more functionalizing agents to form one or more polymers of the formula

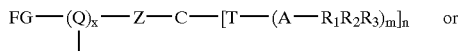

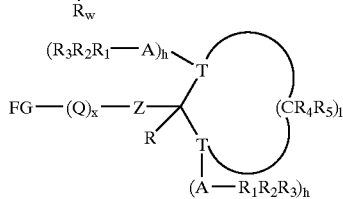

wherein:
  each FG is independently a protected or unprotected functional group;
  each Q is independently a saturated or unsaturated hydrocarbyl group derived by incorporation of one or more conjugated diene hydrocarbons, one or more alkenyl-substituted aromatic compounds, or mixtures of one or more conjugated diene hydrocarbons with one or more alkenylsubstituted aromatic compounds; and
  each x is independently the number of units of conjugated diene hydrocarbons, alkenylsubstituted aromatic compounds, or mixture thereof and ranges from about 10 to about 2000.

15. The process of claim 14, wherein FG is an unprotected functional group and further comprising the step of reacting said unprotected functional group with one or more monomers to form a polymer segment.

16. The process of claim 11, wherein said one or more living polymer anions is reacted with one or more difunctional coupling agents to form one or more polymers of the formula

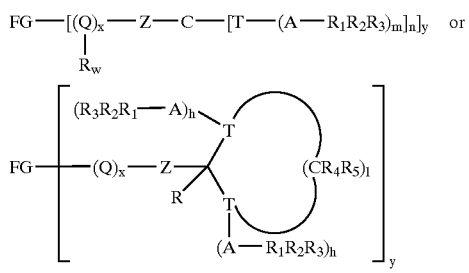

wherein:
- each FG is independently the residue of the difunctional coupling agent;
- each Q is independently a saturated or unsaturated hydrocarbyl group derived by incorporation of one or more conjugated diene hydrocarbons, one or more alkenyl-substituted aromatic compounds, or mixtures of one or more conjugated diene hydrocarbons with one or more alkenylsubstituted aromatic compounds;
- each x is independently the number of units of conjugated diene hydrocarbons, alkenylsubstituted aromatic compounds, or mixture thereof and ranges from about 10 to about 2000; and
- each y is independently 2.

17. The process of claim 11, wherein said one or more living polymer anion is reacted with one or more multifunctional coupling agents to form one or more polymers of the formula

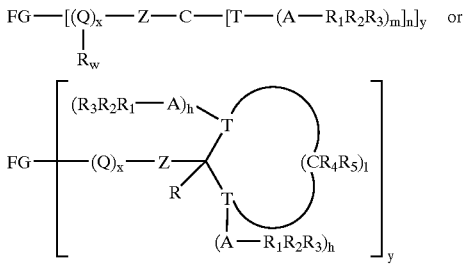

wherein
- each FG is independently the residue of a multifunctional coupling agent;
- each Q is independently a saturated or unsaturated hydrocarbyl group derived by incorporation of one or more conjugated diene hydrocarbons, one or more alkenyl-substituted aromatic compounds, or mixtures of one or more conjugated diene hydrocarbons with one or more alkenylsubstituted aromatic compounds;
- each x is independently the number of units of conjugated diene hydrocarbons, alkenylsubstituted aromatic compounds, or mixture thereof and ranges from about 10 to about 2000; and
- each y is independently 3 to 30.

* * * * *